United States Patent
Lin et al.

(10) Patent No.: US 8,080,697 B2
(45) Date of Patent: Dec. 20, 2011

(54) PROCESS FOR THE PRODUCTION OF ETHYLENE FROM NATURAL GAS WITH HEAT INTEGRATION

(75) Inventors: Yungyi Lin, Riyadh (SA); Mohamed Abdelghani, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 454 days.

(21) Appl. No.: 12/223,145

(22) PCT Filed: Jan. 18, 2007

(86) PCT No.: PCT/EP2007/000417
§ 371 (c)(1),
(2), (4) Date: Mar. 13, 2009

(87) PCT Pub. No.: WO2007/082746
PCT Pub. Date: Jul. 26, 2007

(65) Prior Publication Data
US 2010/0234476 A1    Sep. 16, 2010

(30) Foreign Application Priority Data
Jan. 23, 2006  (EP) .................................... 06001315

(51) Int. Cl.
*C07C 5/08* (2006.01)
(52) U.S. Cl. ........ 585/257; 585/534; 585/535; 585/539; 585/634; 585/259
(58) Field of Classification Search .................. None
See application file for complete search history.

(56) References Cited

U.S. PATENT DOCUMENTS

| | | | |
|---|---|---|---|
| 3,267,170 A | 8/1966 | Aldridge et al. | |
| 3,321,545 A | 5/1967 | Rigney et al. | |
| 3,396,207 A * | 8/1968 | Bartholome et al. | 585/539 |
| 3,647,907 A * | 3/1972 | Sato et al. | 62/114 |
| 4,128,595 A | 12/1978 | Montgomery | |
| 4,725,349 A | 2/1988 | Okamoto et al. | |
| 5,059,732 A * | 10/1991 | Cosyns et al. | 585/259 |
| 5,270,016 A | 12/1993 | Alahy et al. | |
| 5,789,644 A | 8/1998 | Passler et al. | |
| 5,824,834 A | 10/1998 | Bachtler et al. | |
| 5,847,250 A | 12/1998 | Flick et al. | |
| 8,013,196 B2 * | 9/2011 | Mamedov et al. | 585/257 |

(Continued)

FOREIGN PATENT DOCUMENTS

CA       2442657 A1    3/2004

(Continued)

OTHER PUBLICATIONS

Soylemez M S: "On the optimum heat exhanger . . . ", Energy Conversion and Management, Elsevier Science Pub, Oxford, GB, vol. 41, No. 13, (Sep. 2000), p. 1419-1427.

(Continued)

*Primary Examiner* — Tam M Nguyen
(74) *Attorney, Agent, or Firm* — Cantor Colburn LLP

(57) ABSTRACT

The present invention relates to a process for the production of ethylene, comprising the following steps of: (a) thermally converting a feed charge containing methane into acetylene as an intermediate, (b) in-situ hydrogenation of the acetylene produced in step (a) into ethylene by a non-catalytic hydrogen transfer mechanism, characterized by (c) recovering heat from hot effluents obtained in step (b) which may be utilized for different purposes.

16 Claims, 10 Drawing Sheets

U.S. PATENT DOCUMENTS

| | | | |
|---|---|---|---|
| 2004/0065014 A1 | 4/2004 | Christensen et al. | |
| 2005/0048658 A1* | 3/2005 | Johnson et al. | 436/37 |
| 2005/0049445 A1 | 3/2005 | Johnson et al. | |
| 2005/0065391 A1 | 3/2005 | Gattis et al. | |
| 2005/0065392 A1 | 3/2005 | Peterson et al. | |
| 2009/0198090 A1* | 8/2009 | Mamedov et al. | 585/324 |

FOREIGN PATENT DOCUMENTS

| | | |
|---|---|---|
| GB | 921305 A | 3/1963 |
| GB | 958046 A | 5/1964 |

OTHER PUBLICATIONS

International Search Report; International Application No. PCT/EP2007/000417; International Filing Date Jan. 18, 2007; Date of Mailing Jun. 1, 2007; 3 pages.

Written Opinion of the International Searching Authority; International Application No. PCT/EP2007/000417; International Filing Date Jan. 18, 2007; Date of Mailing Jun. 1, 2007; 5 pages.

* cited by examiner

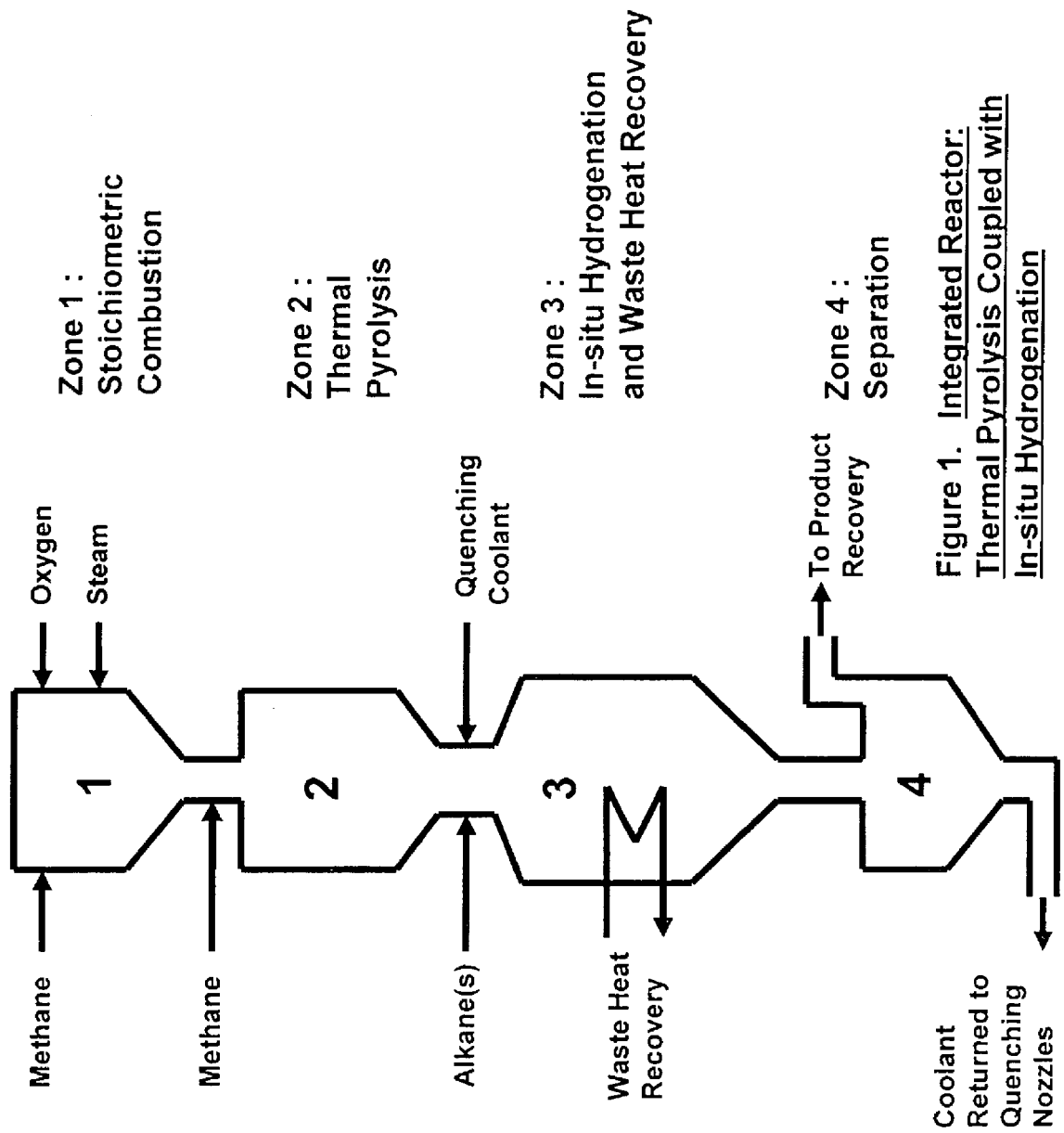
Figure 1. Integrated Reactor: Thermal Pyrolysis Coupled with In-situ Hydrogenation

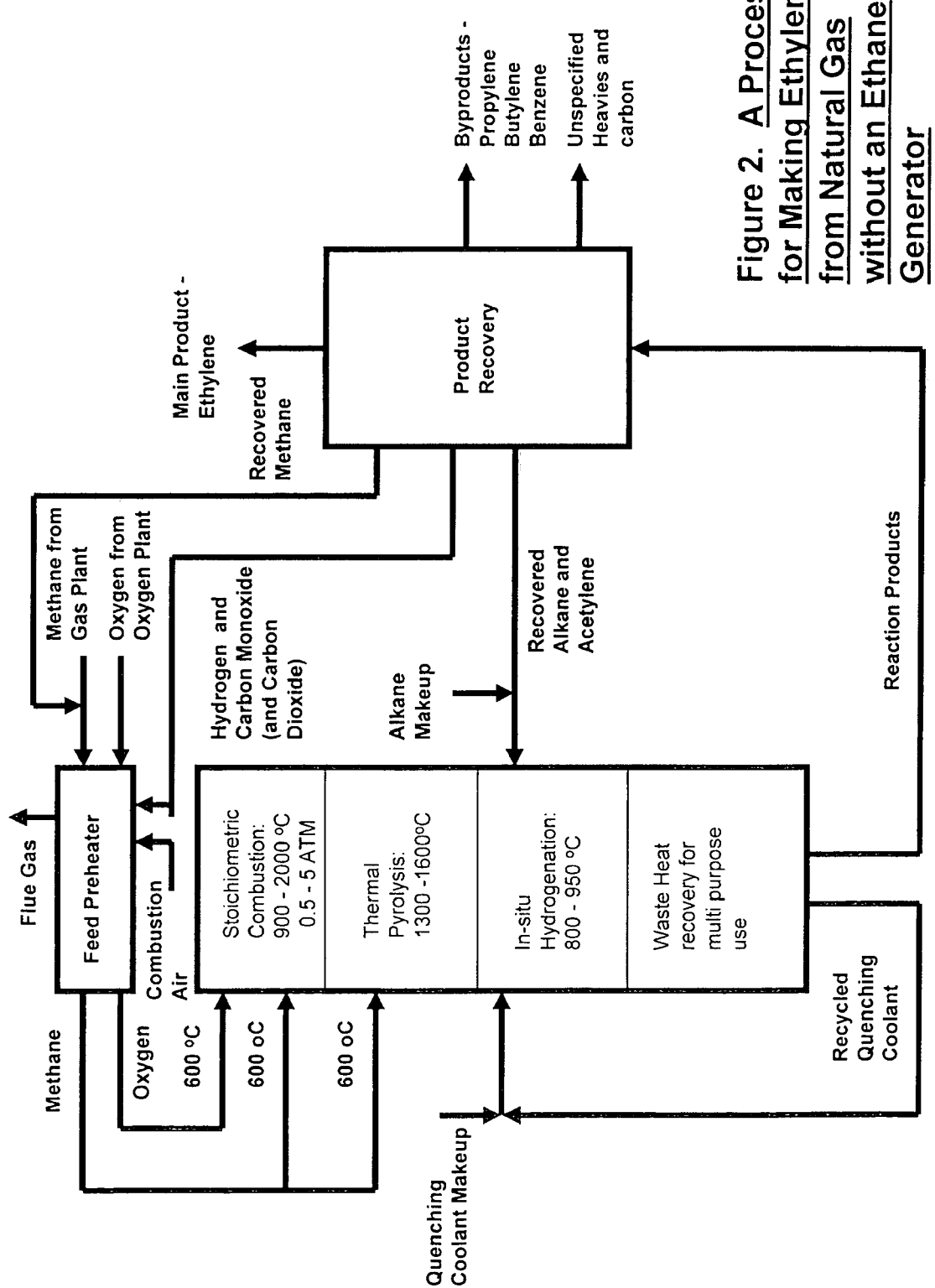
Figure 2. A Process for Making Ethylene from Natural Gas without an Ethane Generator

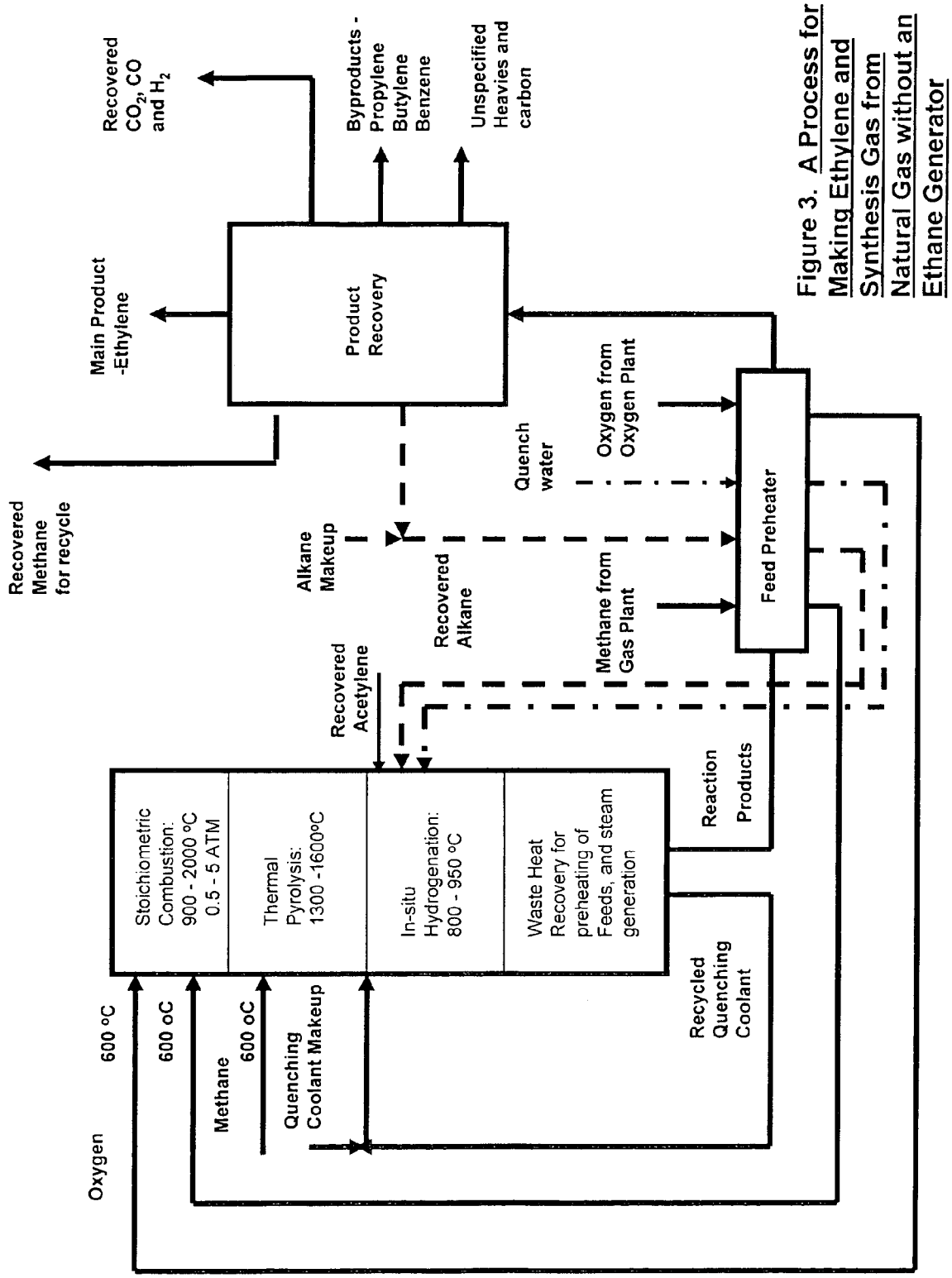
Figure 3. A Process for Making Ethylene and Synthesis Gas from Natural Gas without an Ethane Generator

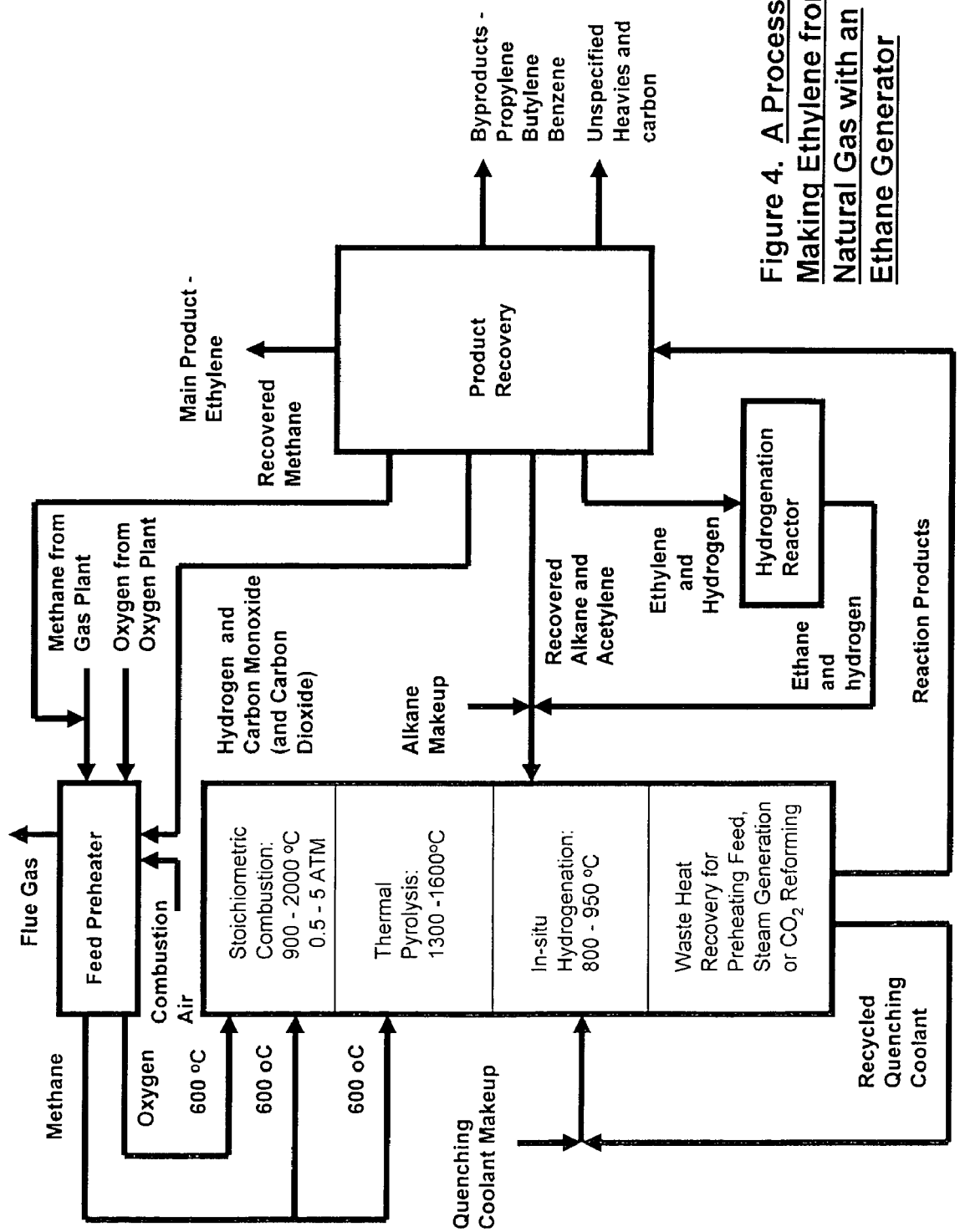
Figure 4. A Process for Making Ethylene from Natural Gas with an Ethane Generator

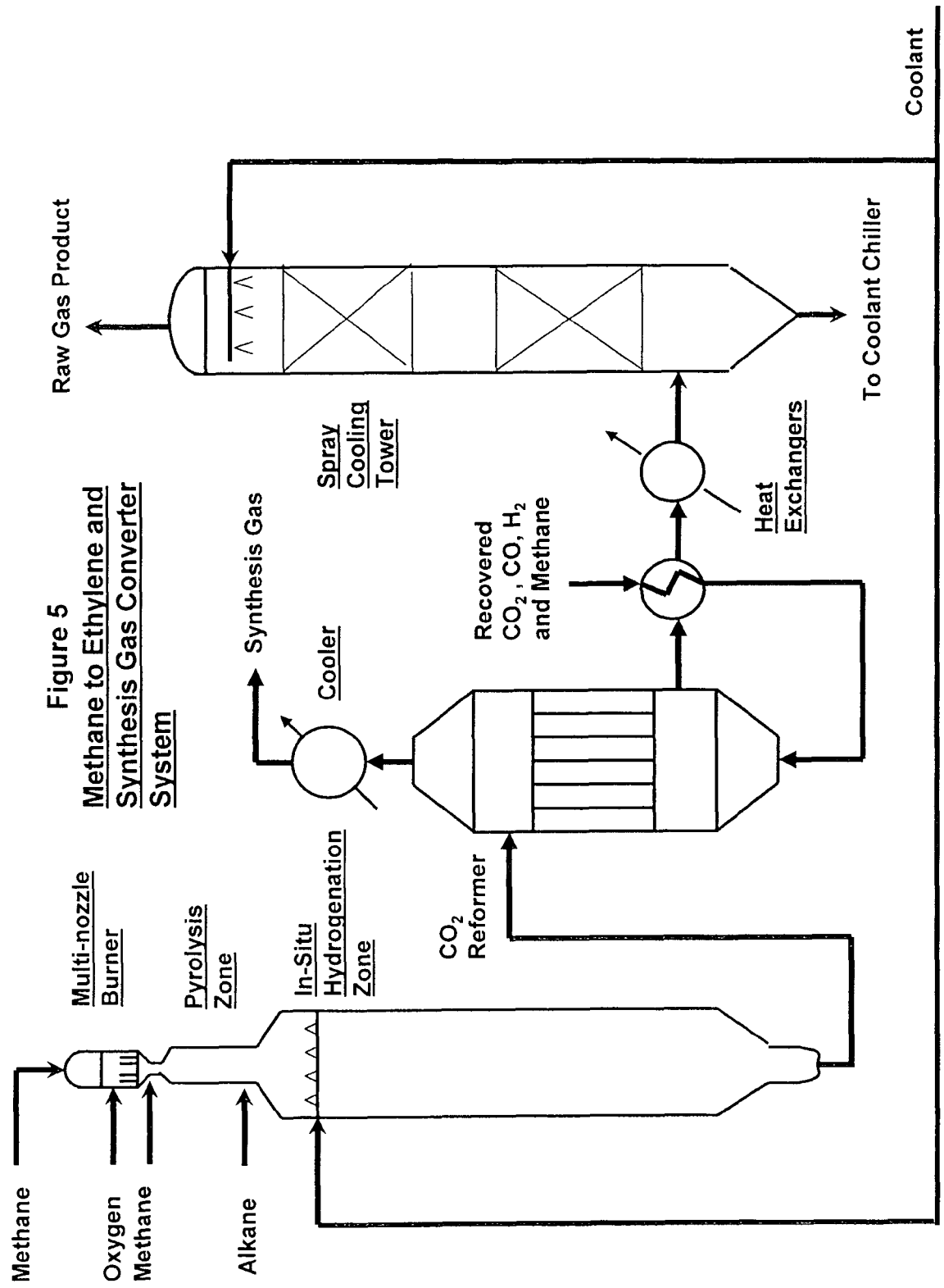

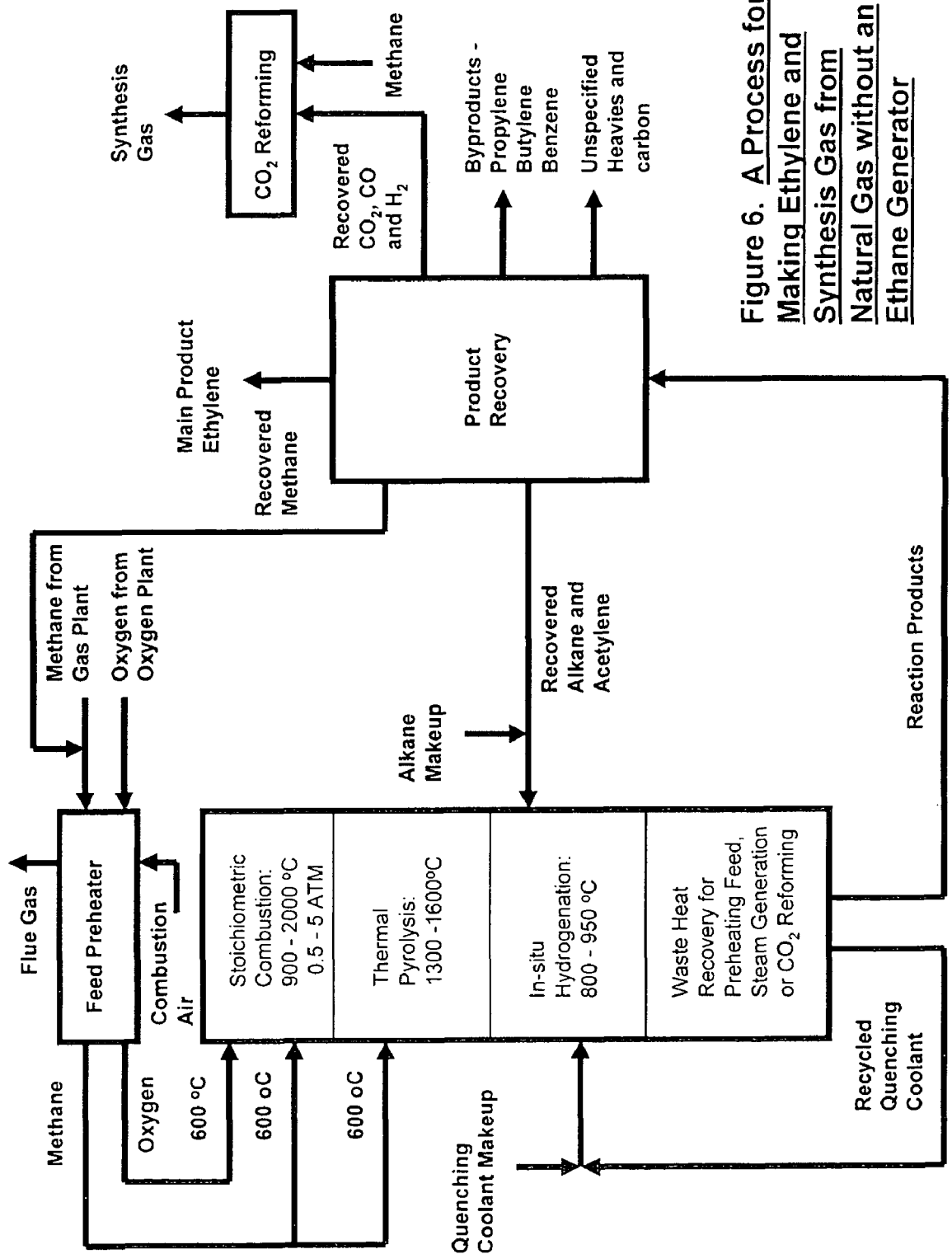
Figure 6. A Process for Making Ethylene and Synthesis Gas from Natural Gas without an Ethane Generator

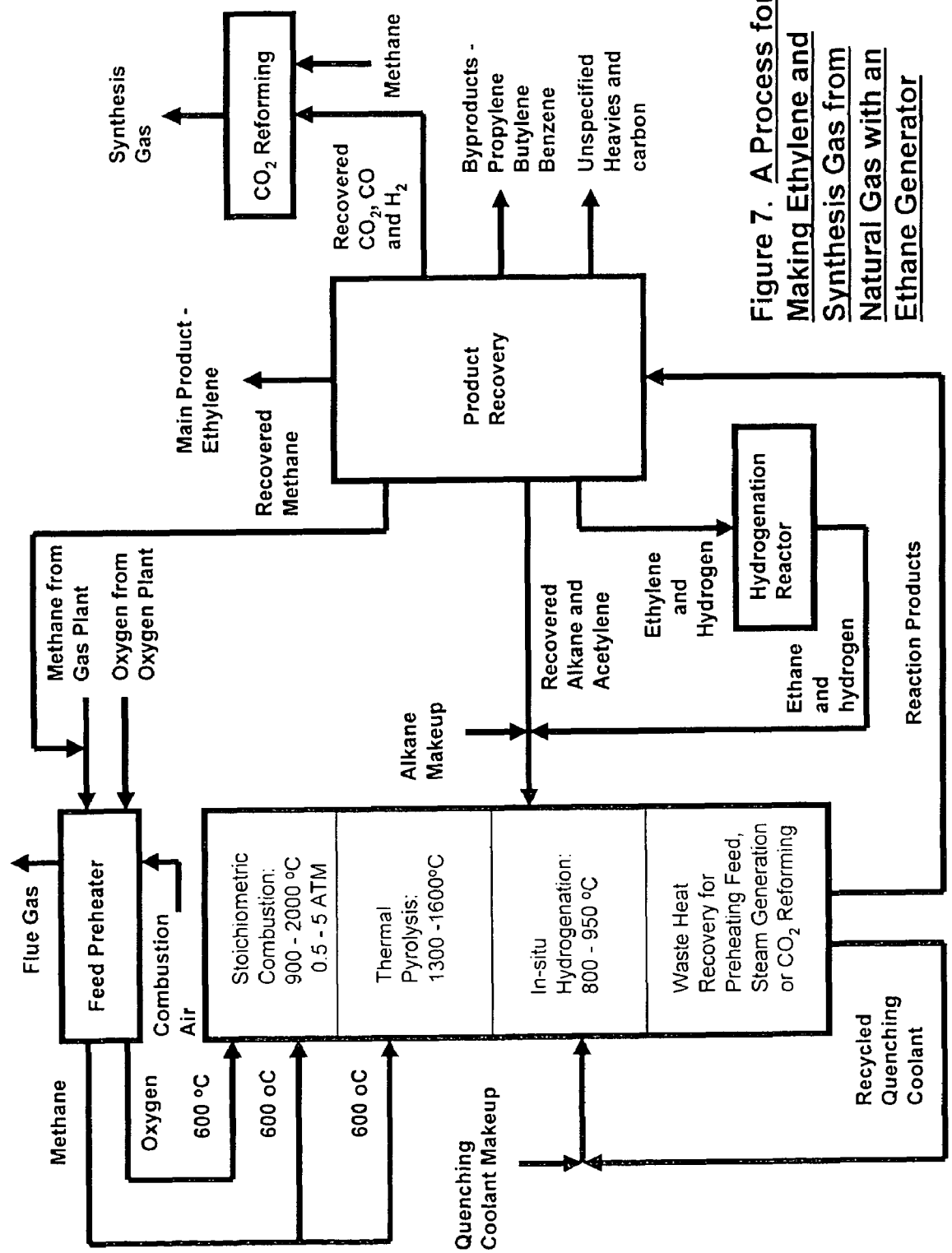
Figure 7. A Process for Making Ethylene and Synthesis Gas from Natural Gas with an Ethane Generator

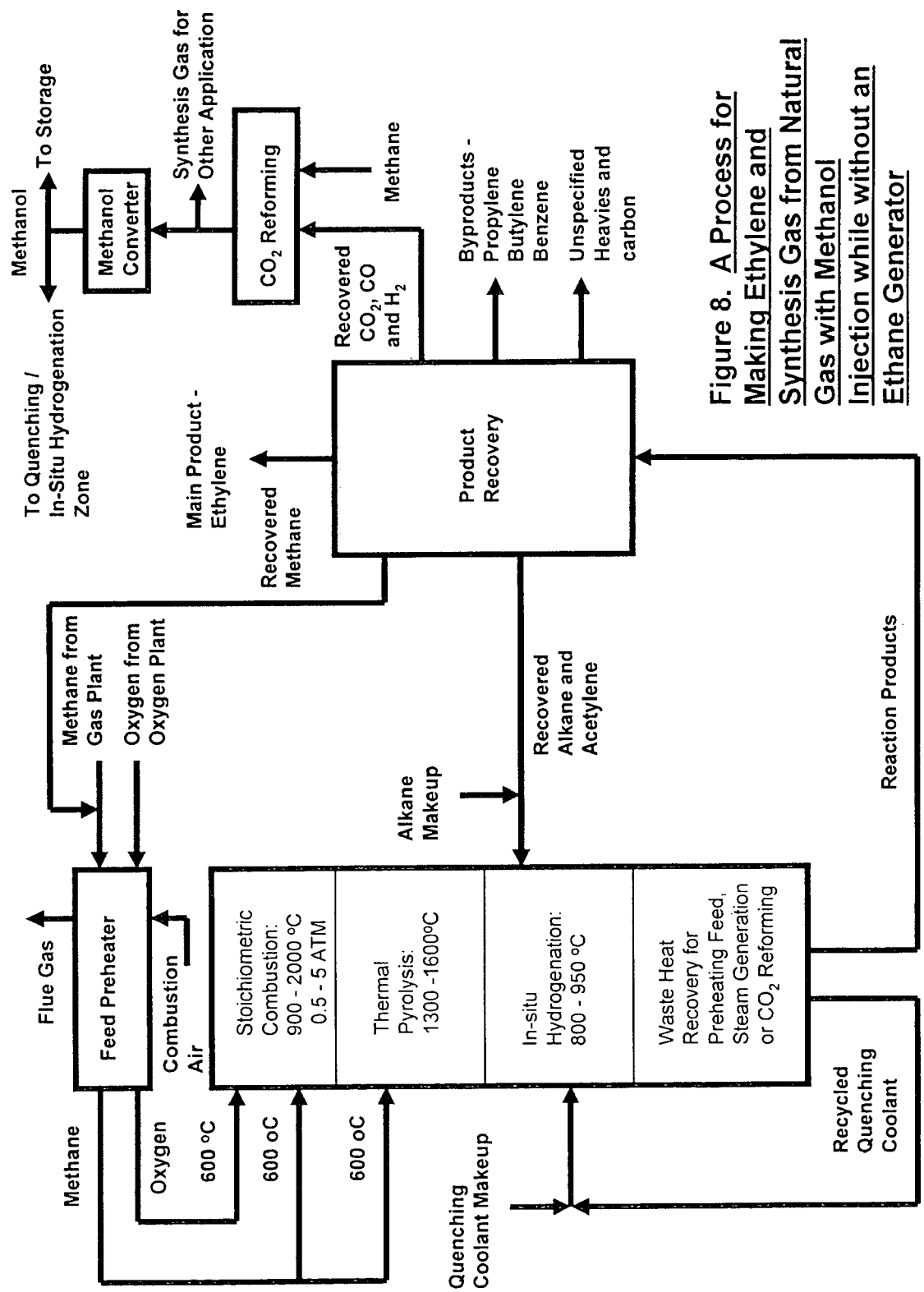
Figure 8. A Process for Making Ethylene and Synthesis Gas from Natural Gas with Methanol Injection while without an Ethane Generator

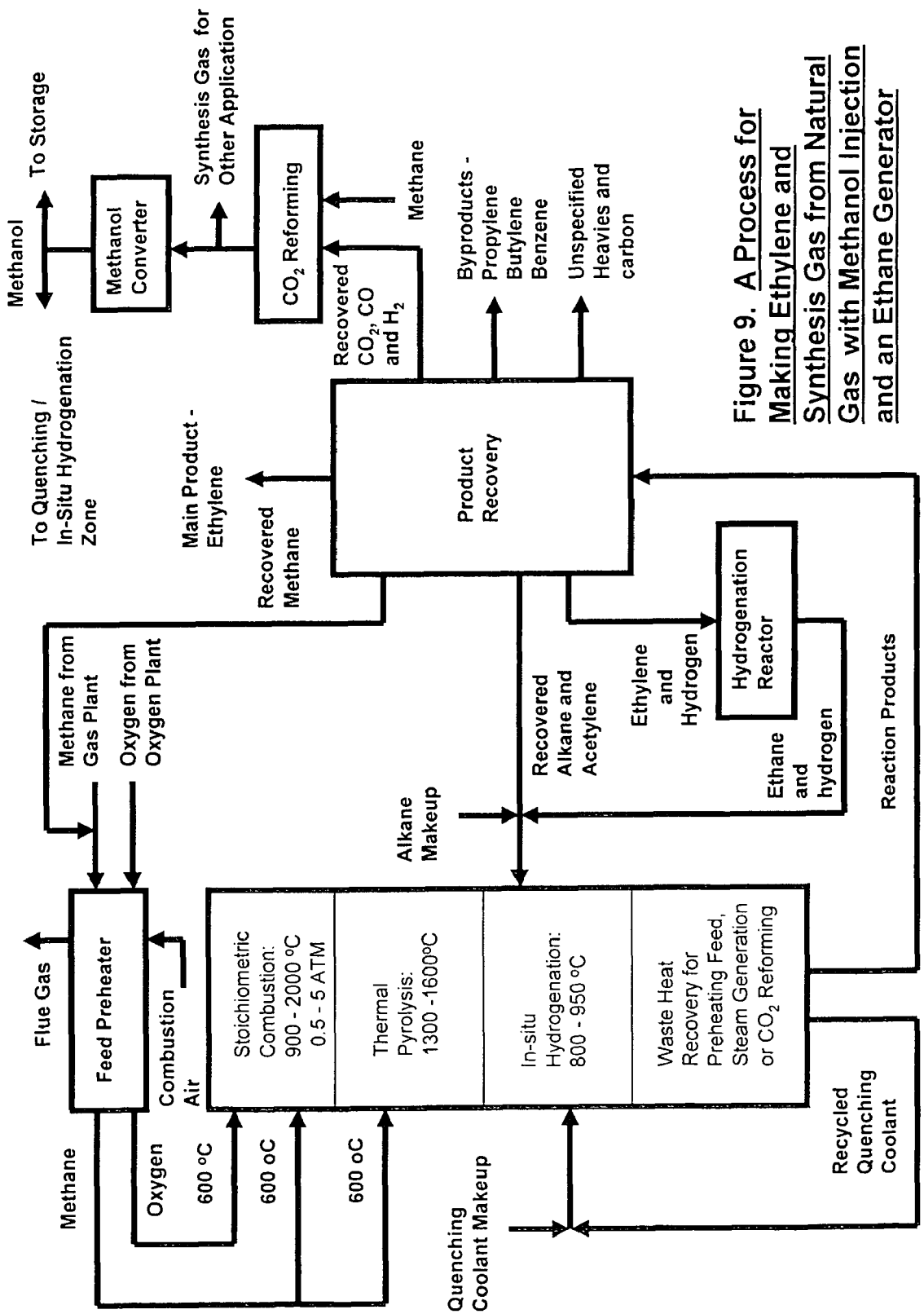
Figure 9. A Process for Making Ethylene and Synthesis Gas from Natural Gas with Methanol Injection and an Ethane Generator

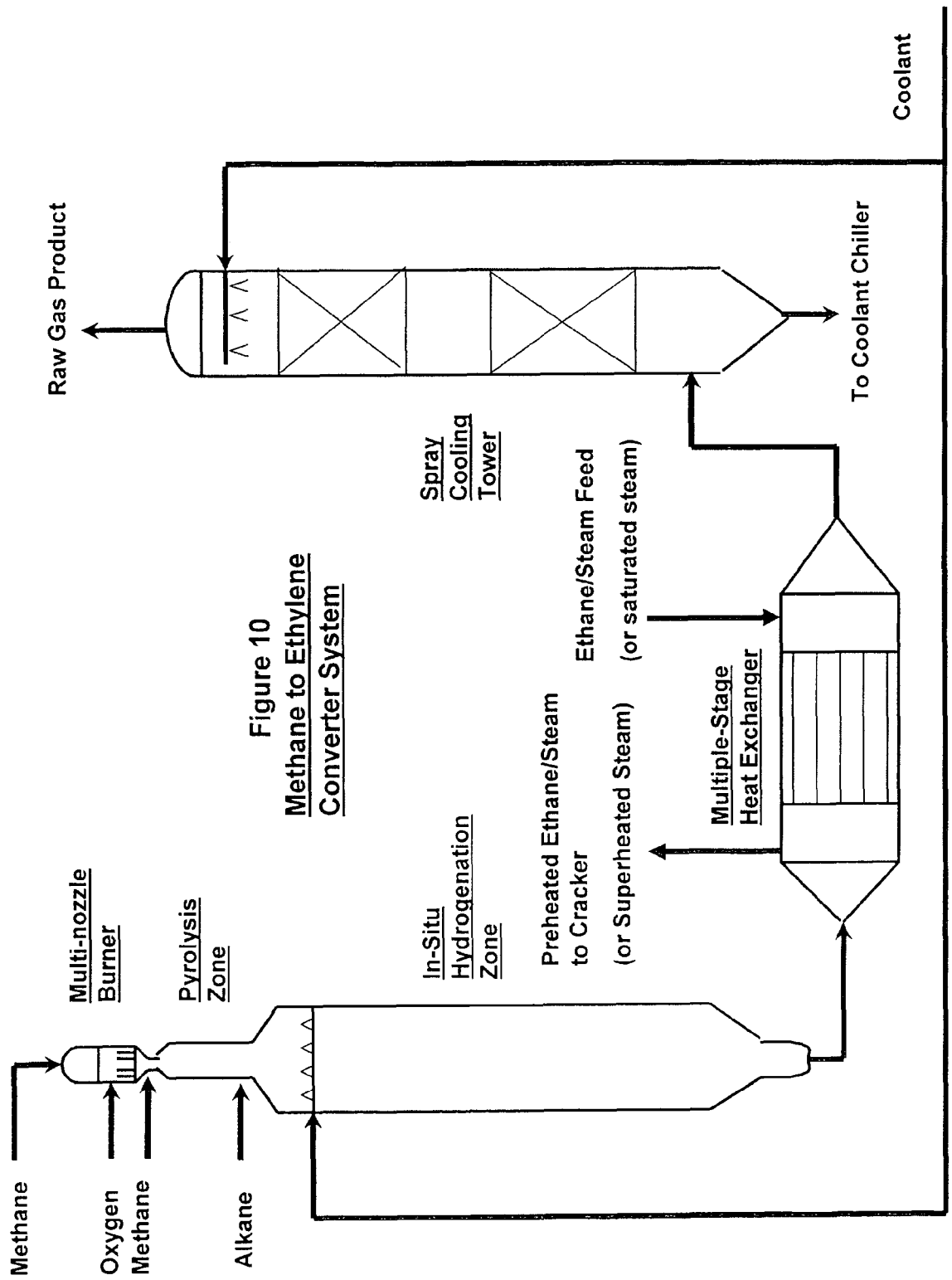

PROCESS FOR THE PRODUCTION OF ETHYLENE FROM NATURAL GAS WITH HEAT INTEGRATION

FIELD OF THE INVENTION

The present invention relates to a process for the production of ethylene, comprising the steps of:
thermally converting a feed charge containing methane into an acetylene containing effluent,
in-situ hydrogenating the acetylene produced in step (a) into ethylene.

PRIOR ART

High-temperature pyrolysis has been used for converting methane to acetylene commercially. It is a proven and well-developed process. Depending on the method used to supply the necessary endothermic heat of pyrolysis, the methane and/or hydrocarbon pyrolysis to acetylene process is broadly categorized into one-step and two-step processes.

The partial oxidation process developed by BASF is the most representative one-step acetylene production process, in which natural gas substantially comprising methane serves for the hydrocarbon feed and pure oxygen as the oxidant. The most recent features and related specifications are disclosed in U.S. Pat. Nos. 5,824,834 and 5,789,644. The general reactor configuration and mechanical design for this single step partial process is described in U.S. Pat. No. 5,789,644. As a whole, the partial oxidation reactor system includes three major parts: the top one is a mixing zone with a special diffuser, the second part (underneath) is a water-jacketed burner immediately followed by a reaction zone, and the final part is a quenching zone using water or heavy oil as a coolant. The key element of this patent is ascribed to the use of a perforated plate to cover the burner for special control purpose. Aside from the description of the general process scheme, some of the critical feed ratios, especially the carbon-to-oxygen ratios are specified in U.S. Pat. No. 5,824,834. According to this patent, the ratio of carbon to oxygen is essential for controlling the soot formation, which cannot be entirely or effectively eliminated from this process.

In the meantime, the ratio of acetylene to synthesis gas in the product stream can be controlled and optimized by this particular feed ratio as well.

Acetylene can also be produced through a two-stage high temperature pyrolysis (HTP) process developed by HOECHST (GB 921,305 and 958,046). This process comprises two main reaction zones followed by a quenching zone. The first reaction zone serves as a stoichiometric combustor to supply the necessary endothermic heat of hydrocarbon pyrolysis taking place in the second reaction zone, into which a fresh hydrocarbon feed such as methane is introduced. In the quenching zone, water or heavy oil is used as a coolant to cool down instantaneously the hot product gas from the pyrolysis zone. Similarly, a certain quantity of carbon will be formed in this two-step pyrolysis process. The acetylene concentration produced in the two step pyrolysis method is about double the acetylene produced in the one stage partial oxidation process. The amount of acetylene produced can also be increased by injection of methanol into the reaction zone during thermal cracking of hydrocarbons between 1200-1000° C. as disclosed by Mitsubishi in U.S. Pat. No. 4,725, 349.

The acetylene thus obtained can be used to make a variety of useful products via different synthesis routes. Notably, the acetylene can be converted to ethylene through a catalytic hydrogenation step. The process for hydrogenation of acetylene to ethylene in the presence of $Pd/Al_2O_3$ catalyst is also well known (U.S. Pat. No. 5,847,250). Such a process step is used primarily for purifying the ethylene product from a steam cracker usually contaminated with typically less than 1.5% of acetylene. This traditional hydrogenation process scheme is not economical for mass production of ethylene from acetylene. Another shortcoming found in using the traditional hydrogenation scheme for this purpose is a high degree of oligomerization of acetylene into heavy hydrocarbons, which are the precursors of green oil and coke formation. Because of these undesirable side reactions, the hydrogenation catalyst is deactivated rapidly and needs to be regenerated from time to time. Furthermore, due to the high exothermic heat of reaction, the reactor temperature may run away readily, thus leading to an unacceptable decline of the catalyst selectivity. In view of these drawbacks and deficiencies, the use of the vapor-phase hydrogenation for the mass production of ethylene from acetylene is deemed to be difficult although it is not impossible.

Notwithstanding, the hydrogenate temperature may be controllable in a liquid-phase reactor, through which an adequate volume of liquid solvent is re-circulated continuously to maintain a steady reaction temperature and thereby reduce the rate of the catalyst deactivation (U.S. Pat. Nos. 4,128,595 and 5,059,732 as well as US Patent Applications 2005/0048658A1 and 2005/0049445A1). In this fashion, the acetylene is dissolved mainly in the solvent. Depending on the type of solvent used, the extent of hydrogenation may vary as illustrated in U.S. Pat. No. 4,128,595. For one instance of this practice, the reaction of hydrogenation has been carried out at 116 to 193° C. over $Pd/Al_2O_3$ catalyst immersed in an inert paraffinic hydrocarbon solvent. In the course of this experiment, the conversion of acetylene was maintained steadily at 99% with a selectivity of 84% for 9 days. However, if DMF solvent was used instead, the conversion of acetylene dropped from 100% to 50% in about 17 hours and the attainable selectivity was only 75%. The results of this experiment revealed the difficulties in attaining the steady-state performance of the particular hydrogenation catalyst.

Similar liquid phase hydrogenation of acetylene using gasoline as a liquid medium has been described in U.S. Pat. No. 5,059,732. Although this method had prolonged the catalyst life, it did give rise to the formation of heavy hydrocarbons as a result of the oligomerization of acetylene.

US Patent Applications 2005/0048658A1 and 2005/0049445A1 offer a method for the hydrogenation of acetylene over Pd based catalyst by using NMP as a liquid solvent. According to these patent applications, the concentration of acetylene dissolved in the solvent is about 4.2% only. Based on this particular information, it is not difficult to foretell that the required reactor size will be uneconomically large for the mass production of ethylene. In addition, this method could not effectively eliminate the oligomerization of acetylene. It still needed a catalyst regeneration step to sustain the desirable activity of catalyst even though the catalyst could remain stable for 6 days (140 hours). Moreover, a pyrolysis process for acetylene production followed by a traditional liquid phase hydrogenation scheme downstream is disclosed. However, the scheme to be implemented not only complicates the process design but also gives a quite limited specific production rate due to the low solubility of acetylene in the solvent.

The catalyst used for the hydrogenation of acetylene to ethylene is susceptible to fouling as a consequence of the inevitable formation of heavy materials in the reactor when the concentration of acetylene exceeds a certain limit. Deactivation of the Pd containing catalyst caused by green oil during the hydrogenation of acetylene was described in literature (R. K. Edvinsson, A. M. Holmgren and Said Irandoust., Ind. Eng. Chem. Res. 1995, 34, 94-100). The authors suggested that a special type of monolithic reactor can be used for the gas/liquid/solid acetylene hydrogenation reaction. In their work, the hydrogenation of acetylene was carried out in the presence of Pd/α-$Al_2O_3$ supported on the surface of monolith in the liquid phase at 40° C. and 20 atm by use of a feed containing 3% of $C_2H_2$, 28% of $C_2H_4$, and 6 to 11% of $H_2$ balanced by $N_2$. For this case, the selectivity to ethylene dropped significantly as the conversion of $C_2H_2$ increased. At 90% conversion of $C_2H_2$, the selectivity of $C_2H_2$ to $C_2H_4$ was found to be 60%. Moreover, the catalyst was not stable when the experiment ran at a continuous basis. After 50 hours, the selectivity of acetylene to ethylene started to decline. In addition, it was observed that the presence of CO in the feed had adverse effect on the catalytic hydrogenation rate so that the hydrogenation stopped completely as the concentration of CO reached 1200 ppm. Apparently, the decrease in the hydrogenation rate was attributed to the CO blocking (or poisoning) of some hydrogen adsorption sites. Thus, it is necessary to install a CO purification unit prior to the traditional catalytic hydrogenation reactor to ensure the stable performance of such catalyst.

As an alternative to the hydrogenation, the concept of hydrogen transfer was mentioned and practiced in some chemical synthesis routes at quite different catalytic reaction conditions (U.S. Pat. Nos. 3,267,170 and 3,321,545). However, the performance of such a process is still constrained by catalyst activity and selectivity. Moreover, it requires a separate hydrogen-transfer reactor associated with a dedicated gas purification unit.

As mentioned earlier, the methane pyrolysis to acetylene is a well-known process. In 1950s and 60s, it had been used for the mass production of acetylene, which then served as the intermediate feed for making vinyl chloride monomer (VCM) and 1,4-butanediol (CHEM SYSTEMS Report on Acetylene—93S14, February 1996, pp. 1). Later on, this particular application faded away due to its unattractive economy.

Recently, there is a renewed interest in using the high-temperature pyrolysis process as the first step for converting natural gas into a liquid mixture, which is then upgraded to gasoline as well as valuable commodity products such as ethylene.

In the natural gas to liquid hydrocarbons (GTL) process such as the one disclosed in US Patent Applications 2005/0065391A1 and 2005/0065392A1, the effluent (i.e. hot gas) of the pyrolysis reactor is normally quenched down from about 1400-1500° C. to a relatively low temperature of 120-250° C. by use of a traditional quenching scheme (CHEM SYSTEMS Report on Acetylene—93S14, February 1996, pp. 7 to 16; U.S. Pat. Nos. 3,396,207 and 3,647,907). The quenching is necessary in this process to prevent the decomposition of acetylene into side products and carbon. By using such a one-step quenching method in the acetylene production plant, the recoverable waste heat becomes only the low-grade heat, thus loosing the overall process efficiency.

New developments are being made in the GTL industry for methane reforming by $CO_2$. In addition, in power and/or chemical plants, new initiatives are being taken in the stack industries to develop a variety of workable schemes to abate the emission of carbon dioxide by recovering and utilizing it, notably, the carbon dioxide reforming process (CA2442657; US Patent application 20040065014 A1). However these endothermic reactions require the investment of a relatively large amount of energy and economic constraints in these cases usually require large scale plants and feed stock.

SUMMARY OF THE INVENTION

It is an object of the present invention to provide a process for the production of ethylene having improved economic, energy and environmental aspects and being highly effective in the conversion of acetylene to ethylene.

This object is achieved in that the hydrogenating is carried out by a non-catalytic reaction by intimately mixing the acetylene containing effluent with an ethane feed, and recovering heat from hot effluents obtained in step (b) and utilize these for different purposes.

In a preferred embodiment at least part of the ethylene obtained is hydrogenated to ethane which together with excess unconverted hydrogen is introduced into step (b) and is used as ethane feed.

In this way process is achieved that is self-sustainable in the ethane feed, needing no make up ethane from external sources.

Preferably this hydrogenation to ethane is carried out in a separate catalytic hydrogenation reactor.

Preferably, the thermal conversion is a pyrolysis or a partial oxidation process.

In one alternative, the pyrolysis process is a two-stage process, preferably a high-temperature pyrolysis (HTP).

In such HTP process, preferably the methane containing feed and oxygen are preheated to 550 to 650° C. and are fed in stoichiometric ratio or with oxygen slightly below stoichiometric ratio into a reactor and are reacted in a combustion zone thereof to form hot gases having a temperature of from 900 to 2000° C. and pressure in the range of from 0.5 to 5 atmospheres, wherein the hot combustion gases are then passed to a pyrolysis zone where additional methane may be introduced to form acetylene and wherein the pyrolysis zone is maintained at a temperature of 1200° C. to 1600° C., wherein the contact time is 3 to 30 milliseconds and the pressure is maintained at from 0.5 to 5 atmospheres.

Most preferably, in the pyrolysis zone, the contact time is 5 to 10 milliseconds and the pressure is maintained at about 2 atmospheres.

In another aspect of the invention, the partial oxidation process is comprised of preheating the methane containing feed and oxygen from 600° C. to 650° C. wherein the oxygen to methane feed ratio is in sub-stoichiometric ratio from 0.5 to 0.9, preferably 0.62, and the reaction zone is at a temperature of from 1200 to 1600° C.

In a preferred embodiment, acetylene is, prior to the in-situ hydrogenation, cooled by using Joule-Thompson effect or partial quenching using a coolant or a combination of both to a temperature of between 800 and 1000° C., preferably 850 and 950° C.

The Joule-Thompson effect can be achieved by a multi-stage expansion.

Such coolant is preferably selected from the group consisting of water, heavy hydrocarbons, natural gas, methanol and mixtures thereof.

The partial quench is preferably achieved by spray injection of the coolant into the acetylene containing gases.

In one preferred embodiment, the heat recovered in step (c) is utilized to preheat at least part of the feed introduced into the process.

The feed preferably comprises methane, oxygen, alkane and methanol.

Carbon dioxide ($CO_2$) obtained in step (a) is in another embodiment preferably transferred to and reformed in a reforming device, wherein the heat recovered in step (c) is utilized for conducting carbon dioxide reforming.

Even preferably, downstream of the carbon dioxide reforming device a methanol synthesis apparatus may be provided where synthesis gas produced in the carbon dioxide reforming device is converted into methanol.

Most preferred, at least part of the methanol obtained is recycled back to step (a) and/or (b).

In a further aspect, the heat recovered in step (c) is transferred to and utilized in an alkane steam cracking plant.

Alternatively, the heat recovered in step (c) may be used to generate superheated steam using a multi tube heat exchanger.

One embodiment is characterized in that at least part of the feed to be introduced into the process is preheated in a preheater using hydrogen and carbon monoxide produced by the process.

Some of the water recovered after step (b) is preferably recycled and preheated to steam for re-injection into the in-situ hydrogenation zone to control the reaction temperature.

Further, unconverted acetylene is preferably separated and recycled back into step (b).

Most preferably, the methane containing feed is natural gas.

According to the present invention, the process for the production of ethylene comprises a step of hydrogenation of acetylene to obtain ethylene, which may be carried out in place, i.e. within the reactor for thermal conversion at a temperature between 800 and 950° C. The concentration of unconverted acetylene in the product gases was experimentally determined to be about 1% only. None or on-measurable coke formation was found in the product gas stream. It is believed that the low amount of acetylene of about 1% only present in the product gases is the reason that stable products without decomposition of acetylene into side products and carbon are obtained. Surprisingly, it was found that the high-grade waste heat from the hot effluents obtained in step (b) can be easily be recovered and utilized for different purposes, thus making the process more economical and attractive than other alternatives developed thus far for the production of ethylene from methane containing feeds, such as natural gas. Thus, the inventive process can be considered as a process with an integrated waste heat recovery scheme and allows high energy savings and less environmental impact.

In the inventive process, the intermediate product acetylene is immediately hydrogenated (or disproportionated) by a non-catalytic in-situ hydrogen transfer mechanism. This is preferably achieved by injection of a desirable amount of hydrocarbon, such as ethane, into step (b) to produce ethylene as the final product. Pyrolysis and hydrogen transfer are performed in one single process unit.

The ethane reacts with the acetylene to produce the ethylene.

Thus, the process of the present invention is based on a revolutionary process design concept. Nearly the entire high-grade heat contained in the hot effluent from the in-situ hydrogenation zone can be recovered for different process heating purposes without using a secondary quenching coolant as disclosed in the prior art. The use of such a high-grade heat recovery scheme not only improves the overall process efficiency significantly but also offers a great flexibility in the process configuration to meet specific economic and environmental-protection goals.

In a preferred embodiment, a self-sustaining ethane supply scheme (via the hydrogenation of ethylene back to ethane) is implemented, in which the unconverted hydrogen is supposedly returned into the hydrogenation step to enhance the hydrogenation product yield.

In summary, by recovering and utilizing the waste heat, operating and capital cost of the plant are significantly reduced.

BRIEF DESCRIPTION OF THE DRAWINGS

Additional advantages and features of the present invention are illustrated in detail below with reference to the examples and the accompanying drawings, wherein:

FIG. 1 shows an integrated reactor for carrying out the inventive process with thermal pyrolysis coupled with in-situ hydrogenation;

FIG. 2 illustrates a process scheme for making ethylene from natural gas according to the invention;

FIG. 3 shows a further process scheme for making ethylene and synthesis gas from natural gas according to the invention;

FIG. 4 shows a further embodiment of a process scheme for producing ethylene according to the invention;

FIG. 5 shows a scheme illustrating a system for conversion of methane to ethylene and synthesis gas;

FIG. 6 shows a further embodiment of a process scheme for producing ethylene according to the invention;

FIG. 7 shows a further embodiment of a process scheme for producing ethylene and synthesis gas according to the invention;

FIG. 8 shows a further embodiment of a process scheme for producing ethylene and synthesis gas according to the invention;

FIG. 9 shows a further embodiment of the process scheme for producing ethylene and synthesis gas according to the invention; and FIG. 10 shows a scheme illustrating a system for converting methane to ethylene.

DETAILED DESCRIPTION OF THE INVENTION

The typical reaction zones for a two-step thermal pyrolysis process immediately followed by an in-situ hydrogenation step are shown in FIG. 1. Basically the stoichiometric combustion of natural gas (methane) with oxygen takes place in zone 1. The combustion hot gas then flows to zone 2, in which it is intimately mixed with a fresh feed of natural gas (methane) to bring up the first key reaction, i.e. methane pyrolysis to acetylene and therein supply the necessary endothermic heat of reaction. Subsequently, the pyrolysis product gas is quenched down to a suitable temperature between 800 and 1000° C. with a controlled volume of water in zone 3, where the in-situ hydrogenation is carried out using a supplementary injection of suitable gas or gas mixture for the reaction. The supplementary gas is typically ethane or its mixture with hydrogen, methanol, water and methane. The product gases flowing out of zone 3 have a temperature typically in the range of 800-950° C. and the concentration of acetylene is less than 1.5%. Accordingly, the waste heat retained in such a gas stream is then recovered by means of traditional heat recovery schemes for a variety of process uses in the downstream.

The process shown in FIG. 2 is considered as a base case where a two-step pyrolysis scheme is implemented. The feeds are preheated in a pre-heater utilizing CO and hydrogen evolving from the reaction product as a fuel to preheat the reactor feeds to 600° C. An oxygen stream is also preheated before feeding to the reactor.

The preheated methane is split into two streams one is fed to mixing zone at a stoichiometric ratio with oxygen feed for complete combustion to supply the necessary heat for the endothermic reaction in the pyrolysis zone. The other methane stream is fed to the pyrolysis zone directly. The combustion, pyrolysis and in-situ hydrogenation zones in sequence show a descending reaction temperature profile as the reaction gas cascades down through the reactor. The combination of the partial water (coolant) quench and the injection of ethane into the reactor serve as a unique process scheme for controlling the in-situ hydrogenation temperature as well as for promoting and enhancing the hydrogen-transfer reaction.

The unconverted acetylene in the product stream can be recycled back to the in-situ hydrogenation zone if necessary. The product gases thus obtained when most of acetylene is converted to ethylene typically have a temperature of 800-950° C. The high-grade heat retained in the product gases can be recovered and utilized as the heat sources for various process schemes downstream as well as upstream of the reactor.

Example 1

The simplest scheme for utilizing the available heat is the one contrived for preheating the feeds of methane, oxygen and ethane to the combustion, pyrolysis and in-situ hydrogenation zones to 600° C. by using an in-line multiple-stage heat exchanger as a feed pre-heater as shown in FIG. 3. Preheating of the feeds to this temperature is necessary in order to achieve efficient combustion and pyrolysis reactions while it is still below the temperature of ignition which occurs at 645° C. A computer simulation result, table 1, for a hypothetical ethylene plant capacity of 167,000 t/y shows that the waste heat recoverable from the in-situ hydrogenation could easily provide the required preheating energy without recycling and burning of hydrogen and CO that are by-products of the pyrolysis. This simplifies the process while adding by-product credit to the process economics. Part of the quench water is used for cooling down the hot pyrolysis gas to required in-situ hydrogenation temperature while other part of water quench is introduced as low pressure steam using the available gas heat to moderate the reaction temperature of the in-situ hydrogenation zone.

TABLE 1

| Gas Enthalpy | Available heat in exit gases from in-situ hydrogenation at 950° C. | Heat requirements for preheating methane, oxygen and ethane feeds to 600° C. | Heat requirement to generate low pressure steam for partial quench |
|---|---|---|---|
| M Kcal/hr | 191.7 | 27.4 | 55.8 |

The use of thermal expansion combined with partial quench can reduce the amount of recycled cooling water or low pressure steam. With an initial upstream pressure of 5 atmospheres a drop in pressure of 3 or 2 atmospheres by thermal expansion over the pyrolysis zone can reduce the water quench required to reach a hydrogenation temperature of 950° C. by 32% or 55% as shown in table 2.

The let down in pressure could be done on a multi stage so that a shock wave is avoided, see Perry's Chemical Engineers' Handbook 6$^{th}$ Ed. P5-32.

TABLE 2

| | No thermal expansion | Expansion over 2 atm. pressure difference | Expansion over 3 atm. pressure difference |
|---|---|---|---|
| Water amount K kg/hr | 23.7 | 16.2 | 10.6 |

Example 2

Ethane feed to the in-situ hydrogenation zone of the pyrolysis reactor is partially converted to other gas products in the product gas. The unconverted ethane, can be recycled back directly to the reactor from the product recovery section while the make up ethane can be supplied from hydrogenating part of the ethylene to ethane using available commercial hydrogenation catalysts. The make up ethane is recycled back together with excess hydrogen. In this way the ethylene production technology can be based only on the availability of methane feed stock as shown in FIG. 4.

Example 3

In attempting to reduce the impact of "greenhouse effect" caused by the carbon dioxide ($CO_2$) emission from the pyrolysis reaction, a carbon dioxide reforming process can be effectively implemented by utilizing the heat of such a high-temperature reaction of the in-situ hydrogenation of acetylene to ethylene. The CO2 reforming with methane is an endothermic reaction with an optimum temperature which falls upon about 850° C. that is at the lower limit of the temperature range of the effluent from the in-situ hydrogenation zone.

Thus, it is feasible to recover a large portion of the sensible heat retained in the in-situ hydrogenation product gases as the necessary endothermic heat for the $CO_2$ reforming purpose. A typical embodiment of the process heat integration concept is shown in FIG. 5 and FIG. 6 represents a corresponding block flow diagram. Such an integrated process offers one of the most attractive operation schemes since all of the $CO_2$ generated in the combustion zone can be converted to useful synthesis gas, thus minimizing the pollution while adding some value to a waste by-product of this process. And also it is quite an effective method of recovering the process waste heat. Computer simulation results based on such an integrated process scheme, Table 3, for the production of 167,000 t/y ethylene plant also confirmed that the heat contained in the product gas after the in-situ hydrogenation took place was sufficient to supply all of the endothermic heat required for the $CO_2$ reforming reaction, in which the $CO_2$ recovered typically from the combustion gas reacts with methane in the presence of steam to become synthesis gas with the molar ratio of $H_2$ to CO about 2 to 1. In addition to this the remaining heat was also found to be sufficient for preheating of feed streams as given in table 3. In this way, the integrated process for the production of ethylene from natural gas, thus, becomes quite a special one with nearly zero-pollution of carbon dioxide as well as the low grade heat.

TABLE 3

| Gas enthalpy | Available heat in exit gases from in-situ hydrogenation at 950° C. | Heat requirement to carry out methane reforming reactions at 850° C. | Heat requirement for preheating of feeds to 600° C. |
|---|---|---|---|
| M Kcal/hr | 191.7 | 52.4 | 27.4 |

An additional hydrogenation reactor may be added to this scheme in order to partly or totally supply the required ethane by hydrogenating a suitable amount of the ethylene in a closed loop around the pyrolysis reactor. The make up ethane is supplied with the excess hydrogen to the in-situ hydrogenation zone as shown in FIG. 7.

Example 4

Since the CO2 reforming reaction can produce variable hydrogen to carbon monoxide ratio of 2 or higher depending on feed ratios of methane to steam to CO2, it becomes exceptionally attractive for adding a methanol synthesis plant, or any other hydrocarbon synthesis plant, downstream where the syngas produced from the CO2 reforming can be combined with what is being produced from the combustion/pyrolysis step to make methanol product as shown in FIG. 8. As mentioned in the prior art above it has been reported that the addition of methanol to the thermal hydrocarbon cracking zone increases the acetylene yield; therefore, part of the methanol may be recycled back to the pyrolysis/in-situ hydrogenation reactor zones with the quench water in order to boost the ethylene yield. In addition, an ethylene hydrogenation reactor may be added to this scheme thereby providing the required ethane for in-situ hydrogenation with some excess hydrogen as a self-sustaining operation unit (FIG. 9) with high ethylene yield.

Example 5

The pyrolysis reactor with the in-situ hydrogenation reaction may also be a part of an alkane steam cracking plant where most of the heat required for heating the alkane and steam is chiefly supplied by the hot effluent from the in-situ hydrogenation section, thus increasing the overall ethylene capacity of the plant while reducing the utility costs substantially. A schematic diagram for such process integration is illustrated in FIG. 10, where the multi-stage heat exchanger serves for preheating ethane and steam used in the alkane steam cracking plant.

Example 6

The heat retained in the hot effluent from the in-situ hydrogenation reaction zone may also be used to generate superheated steam using a multi tube heat exchanger (FIG. 10). The steam thus generated may be utilized for driving the compressors used for the cryogenic separation of the gases in distillation columns downstream.

In another embodiment a BASF type partial oxidation reactor can be used similarly to make acetylene which is then in-situ hydrogenated in a similar hydrogenation zone to produce ethylene, followed by heat recovery.

The features disclosed in the foregoing description, in the claims and in the drawings may, both separately and in any combination thereof, be material for realizing the invention in diverse forms thereof.

The invention claimed is:

1. A process for the production of ethylene, comprising the steps of:
    (a) thermally converting a feed charge containing methane into an acetylene containing effluent,
    (b) in-situ hydrogenating the acetylene produced in step (a) into ethylene characterized in that the hydrogenating is carried out by a non-catalytic reaction by intimately mixing the acetylene containing effluent with an ethane feed, and
    (c) recovering heat from hot effluents obtained in step (b) and utilize these for different purposes.

2. The process according to claim 1, wherein at least part of the ethylene obtained is hydrogenated to ethane which together with excess unconverted hydrogen is introduced into step (b) and is used as ethane feed.

3. The process according to claim 2, wherein the thermal conversion is a pyrolysis or a partial oxidation process.

4. The process according to claim 3, wherein the pyrolysis process is a two-stage process.

5. The process according to claim 4, wherein the pyrolysis process is a high-temperature pyrolysis (HTP), wherein the methane containing feed and oxygen are preheated to 550 to 650° C. and are fed in stoichiometric ratio or with oxygen slightly below stoichiometric ratio into a reactor and are reacted in a combustion zone thereof to form hot gases having a temperature of from 900 to 2000° C. and pressure in the range of from 0.5 to 5 atmospheres, wherein the hot combustion gases are then passed to a pyrolysis zone where additional methane may be introduced to form acetylene and wherein the pyrolysis zone is maintained at a temperature of 1200° C. to 1600° C., wherein the contact time is 3 to 30 milliseconds and the pressure is maintained at from 0.5 to 5 atmospheres.

6. The process according to claim 3, wherein the partial oxidation process is comprised of preheating the methane containing feed and oxygen from 600° C. to 650° C. wherein the oxygen to methane feed ratio is in sub-stoichiometric ratio from 0.5 to 0.9, and the reaction zone is at a temperature of from 1200 to 1600° C.

7. The process according to claim 1, wherein acetylene is, prior to the in-situ hydrogenation, cooled by using Joule-Thompson effect or partial quenching using a coolant or a combination of both to a temperature of between 800 to 1000° C.

8. The process according to claim 7, wherein the Joule-Thompson effect is achieved through a multi stage expansion.

9. The process according to claim 7, wherein the coolant is selected from the group consisting of water, heavy hydrocarbons, natural gas, methanol and mixtures thereof.

10. The process according to claim 1, wherein the heat recovered in step (c) is utilized to preheat at least part of the feed introduced into the process or is transferred to and utilized in an alkane steam cracking plant or is used to generate superheated steam using a multi tube heat exchanger.

11. The process according to claim 2, wherein the ethane feed further comprises methane, oxygen and methanol.

12. The process according to claim 1, wherein carbon dioxide ($CO_2$) is obtained in step (a) and is transferred to and reformed in a reforming device, wherein the heat recovered in step (c) is utilized for conducting carbon dioxide reforming.

13. The process according to claim 12, wherein downstream of the carbon dioxide reforming device a methanol synthesis apparatus is provided where synthesis gas produced in the carbon dioxide reforming device is converted into methanol.

14. The process according to claim 13, wherein at least part of the methanol obtained is recycled back to step (a) and/or (b).

15. The process according to claim 1, wherein at least part of the feed to be introduced into the process is preheated in a pre-heater using hydrogen and carbon monoxide produced by the process.

16. The process according to claim 1, wherein unconverted acetylene is separated and recycled back into step (b).

* * * * *